(12) United States Patent
Watanabe et al.

(10) Patent No.: US 8,773,521 B2
(45) Date of Patent: Jul. 8, 2014

(54) ENDOSCOPE APPARATUS

(75) Inventors: Toshiaki Watanabe, Tokyo (JP); Ryo Karasawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 940 days.

(21) Appl. No.: 12/516,074

(22) PCT Filed: Nov. 22, 2007

(86) PCT No.: PCT/JP2007/072626
§ 371 (c)(1),
(2), (4) Date: May 22, 2009

(87) PCT Pub. No.: WO2008/065955
PCT Pub. Date: Jun. 5, 2008

(65) Prior Publication Data
US 2010/0053312 A1 Mar. 4, 2010

(30) Foreign Application Priority Data
Nov. 28, 2006 (JP) ................................ 2006-320369

(51) Int. Cl.
*A62B 1/04* (2006.01)
(52) U.S. Cl.
USPC ........ 348/65; 348/E7.085; 600/109; 600/178; 600/476; 600/160; 356/318; 356/417
(58) Field of Classification Search
USPC .............. 348/65, E7.085; 600/109, 178, 476, 600/160; 356/318, 417
See application file for complete search history.

(56) References Cited

U.S. PATENT DOCUMENTS

| | | | |
|---|---|---|---|
| 6,388,783 B1* | 5/2002 | Weller-Brophy | 398/82 |
| 2002/0014595 A1* | 2/2002 | Sendai et al. | 250/458.1 |
| 2003/0206301 A1* | 11/2003 | Cline et al. | 356/417 |
| 2004/0186351 A1* | 9/2004 | Imaizumi et al. | 600/160 |
| 2006/0173358 A1* | 8/2006 | Xie | 600/476 |
| 2007/0273877 A1* | 11/2007 | Kawano et al. | 356/318 |
| 2009/0292168 A1* | 11/2009 | Farr | 600/109 |

FOREIGN PATENT DOCUMENTS

| | | |
|---|---|---|
| JP | SHO-61-261713 | 11/1986 |
| JP | HEI-6-27371 | 2/1994 |
| JP | HEI-9-313435 | 12/1997 |
| JP | HEI-11-137512 | 5/1999 |
| JP | 2005-261557 | 9/2005 |

\* cited by examiner

*Primary Examiner* — Thuong Nguyen
(74) *Attorney, Agent, or Firm* — Scully, Scott, Murphy & Presser, P.C.

(57) ABSTRACT

The distal end of an inserted portion, having a simple structure, is reduced in diameter, loss of light incident from a body cavity is reduced, and light from two different directions is observed simultaneously and in a separated fashion. Provided is an endoscope apparatus (1) including an inserted portion (2) to be inserted inside a body cavity; a first dichroic mirror (8), disposed in a distal end portion of the inserted portion (2), that transmits light ($L_4$) in a first wavelength band, which is incident from a longitudinal axial direction and that deflects light ($L_2$) in a second wavelength band, which is incident from a radial direction, in the longitudinal axial direction, thereby multiplexing it with the light ($L_4$) in the first wavelength band; a second dichroic mirror (13) that splits the light ($L_2, L_4$) multiplexed by the first dichroic mirror (8) into each wavelength band; and two image-acquisition units (16, 17) that respectively acquire the light ($L_2, L_4$) in the first and second wavelength bands split by the second dichroic mirror (13).

8 Claims, 9 Drawing Sheets

ENDOSCOPE APPARATUS

TECHNICAL FIELD

The present invention relates to an endoscope apparatus.

BACKGROUND ART

In the related art, there are known endoscopes apparatuses that can observe light incident from a distal end face of an inserted portion and light incident from radially outward (for example, see Patent Documents 1 to 4).

The endoscope apparatus in Patent Document 1 performs observation by switching between light from the longitudinal axial direction and the radial direction by means of a switchable mirror.

The endoscope apparatus in Patent Document 2 employs a structure for making light in a common wavelength band incident from the longitudinal direction and radial direction of the inserted portion via separate image-forming optical systems.

The endoscope apparatus in Patent Document 3 perform observation by multiplexing light with different polarization directions by using a polarizing prism.

The endoscope apparatus in Patent Document 4 performs simultaneous observation of light from the longitudinal direction and the radial direction using a hollow quadrangular pyramid mirror.

Patent Document 1: Japanese Unexamined Patent Application, Publication No. HEI-11-137512
Patent Document 2: Japanese Unexamined Patent Application, Publication No. HEI-9-313435
Patent Document 3: Japanese Unexamined Patent Application, Publication No. SHO-61-261713
Patent Document 4: Japanese Unexamined Patent Application, Publication No. HEI-6-27371

DISCLOSURE OF INVENTION

However, the endoscope apparatus disclosed in Patent Document 1 has a drawback in that, because it acquires light from two directions by switching the mirror, it cannot observe two directions simultaneously.

Also, the endoscope apparatus disclosed in Patent Document 2 has a problem in that the structure is complex because it has separate image-forming optical systems for imaging light from two directions.

The endoscope apparatus disclosed in Patent Document 3 has a problem in that loss light occurs, making it difficult to obtain a bright image, because, of the light incident from the longitudinal axial direction and the radial direction of the inserted portion, only light beams having specific polarization directions are respectively transmitted.

Furthermore, the endoscope apparatus disclosed in Patent Document 4 also has a problem in that, regarding the light incident from the longitudinal axial direction, light passing through a central hole in the quadrangular pyramid mirror is observed, and therefore, the acquired light is restricted by the central hole, which causes loss of light.

The present invention has been conceived in light of the circumstances described above, and an object thereof is to provide an endoscope apparatus in which the distal end of an inserted portion, having a simple structure, can be reduced in diameter, which can reduce the loss of light incident from the body cavity, and which can observe light from two different directions simultaneously and in a separated fashion.

In order to realize the object described above, the present invention provides the following solutions.

The present invention provides an endoscope apparatus including an inserted portion to be inserted inside a body cavity; a first dichroic mirror, disposed in a distal end portion of the inserted portion, that deflects light in a first wavelength band, which is incident from a radial direction, in a longitudinal axial direction and that transmits light in a second wavelength band, which is incident from the longitudinal axial direction, thereby multiplexing it with the light in the first wavelength band; a second dichroic mirror that splits the light multiplexed by the first dichroic mirror into each wavelength band; and two image-acquisition units that respectively acquire the light in the first and second wavelength bands split by the second dichroic mirror.

According to the present invention, light in the first wavelength band, which is incident from radially outward of the inserted portion, is deflected in the longitudinal direction by the first dichroic mirror disposed at the distal end of the inserted portion, whereas light in the second wavelength band, which is incident on the distal end of the inserted portion from the longitudinal axial direction, is transmitted through the first dichroic mirror to be multiplexed with the light in the first wavelength band. Because the first dichroic mirror transmits or deflects all of the light having specific wavelength bands, irrespective of the polarization state of the incident light, no light loss occurs in the specific wavelength band to be observed. The multiplexed light in the first and second wavelength bands is split by the second dichroic mirror and is acquired by respective image-acquisition units. Thus, it is possible to observe the light from two different directions simultaneously and is a separated fashion.

In the above-described invention, an image combining unit that combines images acquired by the two image-acquisition units may be provided.

With this arrangement, by operating the image combining unit, it is possible to combine the images of light from two directions which are simultaneously acquired and to observe them in an associated manner.

In the above-described invention, the first dichroic mirror may be conical.

With this arrangement, for the light incident from the radial direction, it is possible to acquire an image of the light around the entire periphery in the circumferential direction of the inserted portion with the conical first dichroic mirror.

In the above-described invention, the first dichroic mirror may be provided with a flat reflecting surface that deflects light from one direction in the radial direction and a rotating device that rotates the reflecting surface about a longitudinal axis of the inserted portion.

With this arrangement, by operating the rotating device, it is possible to rotate the reflecting surface of the first dichroic mirror about the longitudinal axis and to acquire an image of the light around the entire periphery in the circumferential direction of the inserted portion.

In the above-described invention, an illumination unit that radiates illumination light towards the body cavity may be provided in the distal end portion of the inserted portion.

With this arrangement, by operating the illumination unit, the illumination light is radiated towards the body cavity, and light is emitted from the inner surface of the body cavity in response to this illumination light.

For example, if the illumination light is excitation light, because fluorescence in a specific wavelength band is generated by excitation of a fluorescent substance present inside the wall of the body cavity, by setting the transmission wavelength band of the first dichroic mirror to the wavelength band of this fluorescence, it is possible to acquire an image of the fluorescence transmitted in the longitudinal axial direction. Also, by setting the reflection wavelength band of the first dichroic mirror to the wavelength band of this fluorescence, it is possible to acquire an image of this fluorescence incident from the radial direction.

If the illumination light is visible light of a specific wavelength band, by setting the wavelength band of visible light reflected at the inner surface of the body cavity to the transmission or reflection wavelength band of the first dichroic mirror, it is possible to acquire a reflected-light image frontward of the distal end of the inserted portion or a reflected-light image outward in the radial direction.

In the above-described invention, an illumination unit that radiates illumination light towards the body cavity may be provided; the illumination unit may include a light source disposed at a base end of the inserted portion and a light guide through which light from the light source propagates to the distal end of the inserted portion; and the first dichroic mirror may deflect light in a wavelength band radiated radially outward and light in a wavelength band incident from radially outward and transmit light of other wavelength bands.

With this arrangement, the light emitted from the light source disposed at the base end of the inserted portion is propagated via the light guide to the distal end of the inserted portion and is incident on the first dichroic mirror disposed at the distal end of the inserted portion, and thereby, light in part of the wavelength band is deflected by the first dichroic mirror to be emitted radially outward, and the remaining light is transmitted through the first dichroic mirror to be emitted in the longitudinal axial direction. By using a device that multiplexes light of multiple wavelengths as the light source, it is also possible to split the illumination light into each wavelength band with the first dichroic mirror and to radiate them in different directions.

In the above-described invention, an image-forming unit that images the light multiplexed by the first dichroic mirror may be provided at a central portion, in the radial direction, of the inserted portion; the light guide may be disposed outward, in the radial direction, of the image forming unit; and the distal end of the light guide may be disposed at an angle towards the vicinity of the center of the first dichroic mirror.

With this configuration, the light from the light source is guided to the distal end of the inserted portion via the light guides disposed around the inserted portion, and is thereafter divided into each wavelength band by the first dichroic mirror to be respectively radiated in the longitudinal axial direction and the radial direction of the inserted portion. On the other hand, the light beams in different wavelength bands which are incident on the inserted portion from the longitudinal axial direction and the radial direction of the inserted portion are multiplexed by the first dichroic mirror and are incident on the image-forming unit disposed at the center, in the radial direction, of the inserted portion. In this case, by inclining the distal end of the light guide towards the vicinity of the center of the first dichroic mirror, the light transmitted through the first dichroic mirror can be radiated towards the central region frontward of the inserted portion, and a bright image can be acquired.

In the above-described invention, the inserted portion may be a capsule provided, in the interior thereof, with the first dichroic mirror, the second dichroic mirror, and the two image-acquisition units.

With this arrangement, the burden placed on the examination subject when inserting the inserted portion into the body cavity and during image acquisition can be reduced, and it is possible to acquire images of and observe the inside of the body cavity without restricting the activity of the examination subject by the endoscope apparatus.

According to the present invention, an advantage is afforded in that, the distal end of the inserted portion, having a simple structure, can be reduced in diameter, loss of light incident from the body cavity can be reduced, and light from two different directions can be observed simultaneously and in a separated fashion.

EXPLANATION OF REFERENCE SIGNS

Figure 1:
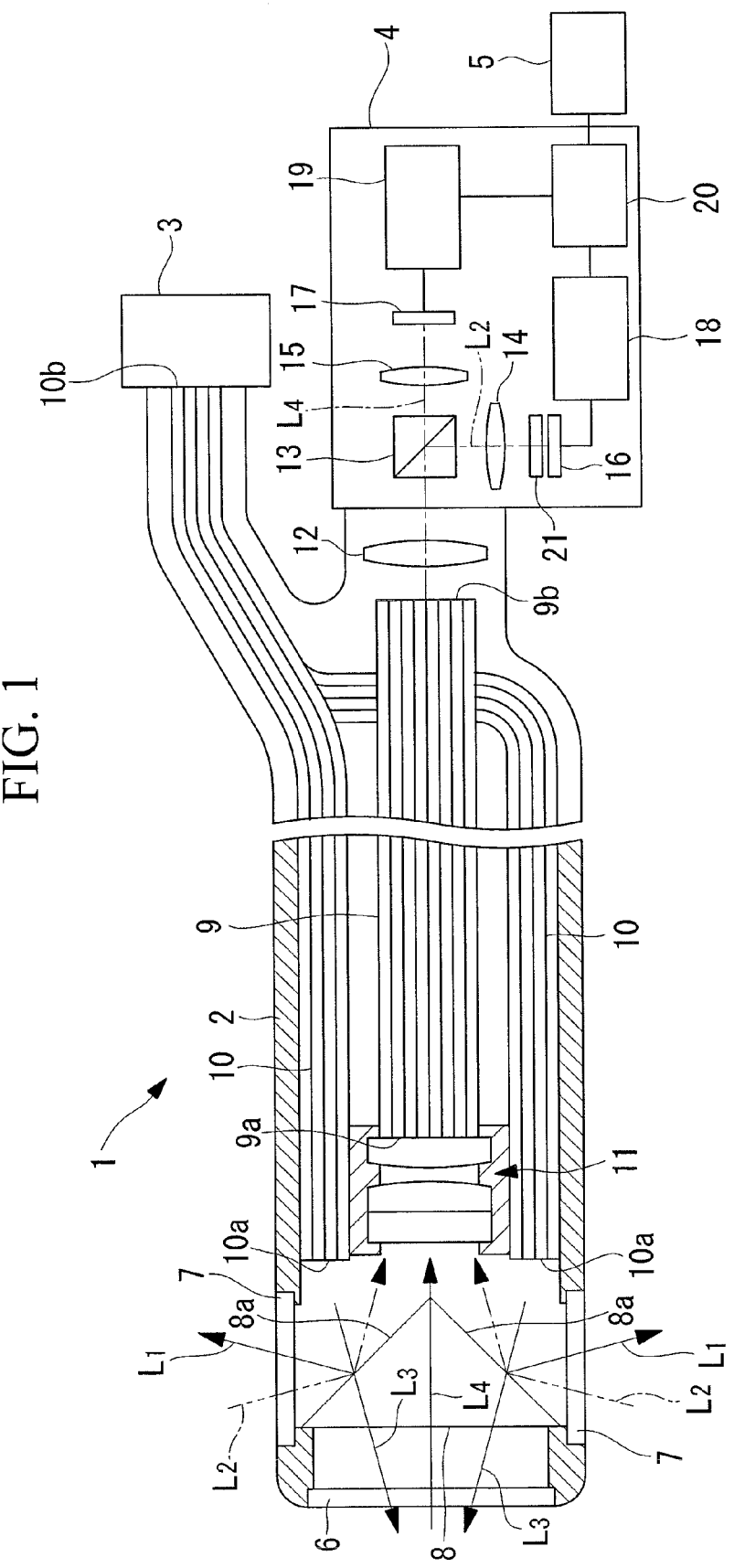
FIG. 1 is an overall configuration diagram schematically showing the endoscope apparatus according to an embodiment of the present invention.

A: body cavity
$L_2$: fluorescence (light in second wavelength band)
$L_4$: reflected light (light in first wavelength band)
1: endoscope apparatus
2: inserted portion
3: light source
8: dichroic conical mirror (first dichroic mirror)
10: light guide
11: image-forming optical system (image-forming unit)
13: dichroic mirror (second dichroic mirror)

16, 17: image-acquisition device (image-acquisition unit)
20: image combining unit
22: light source (illumination unit)
23: excitation light source (illumination unit)
24a: reflecting surface
25: hollow shaft motor (rotating device)
26: battery
27: transmitter
28: light source (white LED)

BEST MODE FOR CARRYING OUT THE INVENTION

An endoscope apparatus 1 according to an embodiment of the present invention will be described below with reference to FIGS. 1 to 3.

As shown in FIG. 1, the endoscope apparatus 1 according to this embodiment includes a long, narrow inserted portion 2 that is inserted inside a body cavity, a light source 3 connected at the base end of the inserted portion 2, an image-acquisition unit 4 connected to the same base end of the inserted portion 2, and a display unit 5 connected to the image-acquisition unit 4.

The inserted portion 2 includes transparent windows 6 and 7 in the distal end face and around the entire outer circumference of the distal end portion thereof. A cone-shaped dichroic conical mirror (first dichroic mirror) 8 is disposed in the distal end portion of the inserted portion 2 with its bottom surface facing the window 6 at the distal end of the inserted portion 2. The dichroic mirror 8 has optical thin films (not shown in the drawing), formed on a conical surface 8a, that reflect excitation light $L_1$ and fluorescence $L_2$ in a first wavelength band and that transmit light $L_3$ and $L_4$ in another wavelength band (second wavelength band).

When the excitation light $L_1$ in the first wavelength band is incident on the dichroic conical mirror 8 from the conical surface 8a side, the excitation light $L_1$ is deflected at the conical surface 8a and is directed radially outward. By making the excitation light $L_1$ incident on substantially the entire conical surface 8a, the excitation light L1 is emitted in a radiating manner around substantially the entire periphery in the circumferential direction and irradiates an inner surface of the surrounding body cavity via the window 7 provided in the side wall of the inserted portion 2. The fluorescence $L_2$ generated at the inner wall of the body cavity as a result of irradiation with the excitation light $L_1$ enters the inserted portion 2 via the window 7 provided in the side wall of the inserted portion 2, whereupon it is deflected at the conical surface 8a of the dichroic conical mirror 8 to be directed in the longitudinal axial direction.

When illumination light $L_3$ in the second wavelength band which is different from the first wavelength band is incident towards the conical surface 8a, the illumination light $L_3$ passes undeflected through the conical surface 8a of the dichroic conical mirror 8 in the longitudinal direction and irradiates the inner surface of the body cavity disposed in front of the inserted portion 2 via the window 6 provided at the distal end of the inserted portion 2. Because the reflected light $L_4$ of the illumination light $L_3$ at the inner surface of the body cavity is also in the second wavelength band, it passes through the dichroic conical mirror 8 from the distal end of the inserted portion 2 and directly enters the inserted portion 2. As a result, the fluorescence $L_2$ in the first wavelength band which is incident from radially outward of the inserted portion 2 and the reflected light $L_4$ in the second wavelength band which is incident from the longitudinal axial direction are multiplexed by the dichroic conical mirror 8.

The inserted portion 2 is equipped with an image guiding fiber 9 at the center position in the radial direction, along the longitudinal direction thereof, and a plurality of light guide fibers 10 are arranged in the circumferential direction radially outward of the image guiding fiber 9. Between the tip of the image guiding fiber 9 and the conical surface 8a of the dichroic conical mirror 8 is provided an image-forming optical system 11 that images the fluorescence $L_2$ and the reflected light $L_4$, multiplexed by the dichroic conical mirror 8, at an end face 9a of the image guiding fiber 9.

The inserted portion 2 is equipped, at the base end thereof, with a collimator lens 12 that opposes an end face 9b of the image guiding fiber 9.

The light source 3 is coupled to end faces 10b of the light guide fibers 10 at the base end of the inserted portion 2 and multiplexes the excitation light $L_1$ in the first wavelength band and the illumination light $L_3$ in the second wavelength band to make them incident on the end faces 10b of the light guide fibers 10.

The image-acquisition unit 4 includes a dichroic mirror (second dichroic mirror) 13 that splits the light formed into a substantially collimated beam by the collimator lens 12 into the fluorescence $L_2$ in the first wavelength band and the reflected light $L_4$ in the second wavelength band; focusing lenses 14 and 15 that focus the respective beams split by the dichroic mirror 13; image-acquisition devices 16 and 17, such as CCDs, whose imaging surfaces are disposed at the focal planes of the focusing lenses 14 and 15; image generating units 18 and 19 that generate a side-view image and a straight-view image on the basis of image information obtained by the image-acquisition devices 16 and 17; and an image combining unit 20 that combines the side-view image and the straight-view image generated by these image generating units 18 and 19. Reference numeral 21 in the figure is an excitation-light cut filter.

The operation of the thus-configured endoscope apparatus 1 according to this embodiment will be described below.

With the endoscope apparatus 1 according to this embodiment, the excitation light $L_1$ and the illumination light $L_3$ generated in the light source 3 are incident on the end faces 10b of the light guide fibers 10 in a multiplexed state and propagate inside the light guide fibers 10 to be guided to the distal end portion of the inserted portion 2. Then, of the excitation light $L_1$ and the illumination light $L_3$ emerging from the distal end faces 10a of the light guide fibers 10, the excitation light $L_1$ having a wavelength in the first wavelength band is reflected at the conical surface 8a of the dichroic conical mirror 8 and is directed radially outward. On the other hand, the illumination light $L_3$ having a wavelength in the second wavelength band is transmitted through the dichroic conical mirror 8 and is directed straight through in the longitudinal axial direction.

Figure 2:
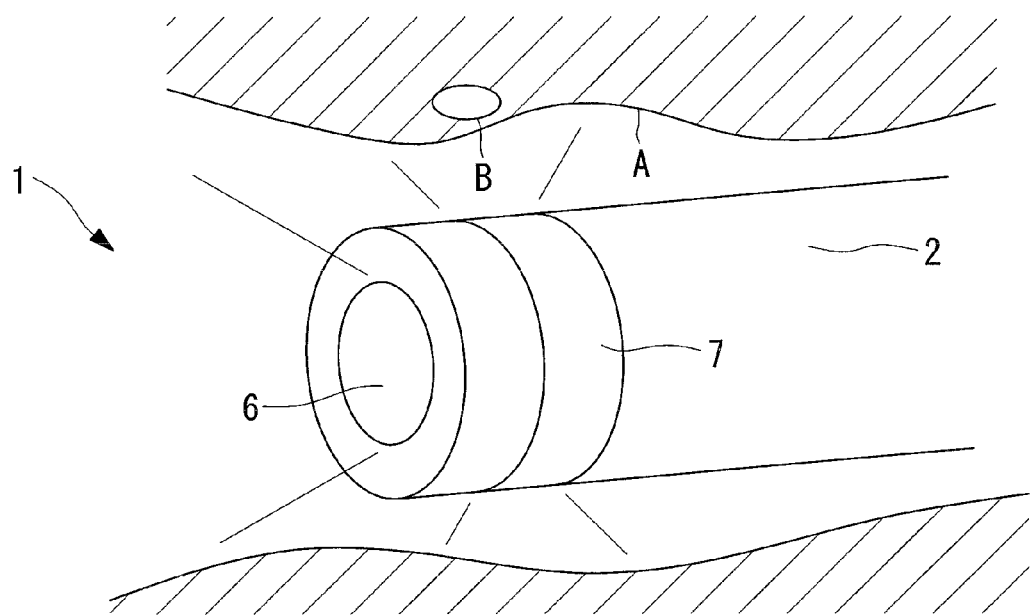
FIG. 2 is a perspective view showing a distal end portion of an inserted portion of the endoscope apparatus in FIG. 1 inserted inside a body cavity.

As shown in FIGS. 1 and 2, the excitation light $L_1$ directed radially outward by the dichroic conical mirror 8 is transmitted through the window 7 provided around the entire circumference in the wall of the distal end portion of the inserted portion 2 to be emitted radially outward from the inserted portion 2 and irradiates the inner wall of the body cavity A disposed radially outward. A fluorescent substance in the inner wall of the body cavity A irradiated by the excitation light $L_1$ is excited, thereby generating the fluorescence $L_2$ having a wavelength in the first wavelength band. The fluorescence $L_2$ generated at the inner wall of the body cavity A enters the inserted portion 2 via the window 7. Because the fluorescence $L_2$ has a wavelength in the first wavelength band, close to the excitation light $L_1$, it is reflected in the longitudinal axial direction by the conical surface $8a$ of the dichroic conical mirror 8.

On the other hand, the illumination light $L_3$ having a wavelength in the second wavelength band, which is transmitted through the dichroic conical mirror 8, is transmitted through the transparent window 6 provided in the distal end face of the inserted portion 2 and emerges from the distal end of the inserted portion 2 substantially in the longitudinal axial direction. The emerging illumination light $L_3$ irradiates the inner wall of the body cavity A disposed in front of the distal end face of the inserted portion 2. The reflected light $L_4$ reflected at the inner wall of the body cavity A enters the inserted portion 2 via the same window 6 and passes straight through the dichroic conical mirror 8 in the longitudinal axial direction.

Accordingly, the fluorescence $L_2$ in the first wavelength band, from radially outward of the inserted portion 2, and the reflected light $L_4$ in the second wavelength band, from the front in the longitudinal axial direction, are multiplexed by the dichroic conical mirror 8. The multiplexed fluorescence $L_2$ and reflected light $L_4$ are focused upon passing through the image-forming optical system 11 and are imaged onto the end face $9a$ of the image guiding fiber 9.

The multiplexed light incident on one end face in the image guiding fiber 9 propagates in the image guiding fiber 9 and emerges from the other end face $9b$ disposed at the base end of the inserted portion 2. Then the light emerging from the other end face $9b$ of the image guiding fiber 9 is converted to a substantially collimated beam by the collimator lens 12 and enters the image-acquisition unit 4.

The light entering the image-acquisition unit 4 is incident on the dichroic mirror 13 and is thereby split once more into the fluorescence $L_2$ in the first wavelength band and the reflected light $L_4$ in the second wavelength band. The split fluorescence $L_2$ and reflected light $L_4$ are focused by the respective focusing lenses 14 and 15 and are captured by the image-acquisition devices 16 and 17. Returning excitation light $L_1$ reflected at the inner wall of the body cavity A is also contained in the fluorescence $L_2$, but because it is blocked by the excitation-light cut filter 21 disposed in front of the image-acquisition device 16, it is prevented from being incident on the image-acquisition device 16.

The image information obtained by the image-acquisition devices 16 and 17 is sent to the side-view image generating unit 18 and the straight-view image generating unit 19, respectively, thereby generating a side-view image $G_2$ and a straight-view image $G_1$. Because the straight-view image $G_1$ is an image in which the interior of the body cavity A is viewed from one direction in the longitudinal axial direction, it can be displayed as is in the form of a two-dimensional image. On the other hand, because the side-view image $G_2$ is a cylindrical-surface image acquired over the entire circumference radially outward of the inserted portion 2, in order to display it as a two-dimensional image, a technique for unfolding it into a strip or a technique for converting it to a ring-shaped image, as shown in FIG. 3, should be employed.

Figure 3:
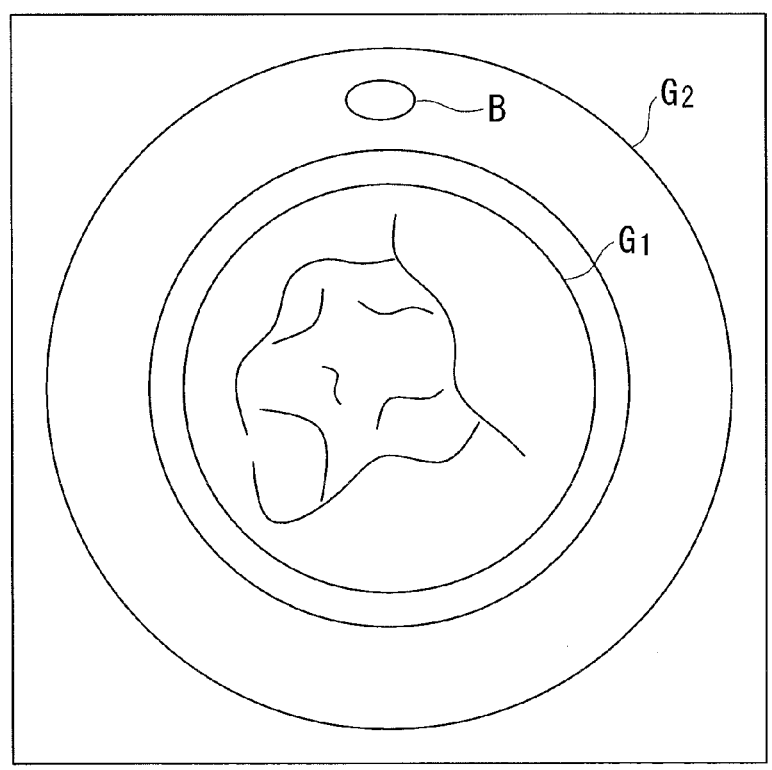
FIG. 3 is a diagram showing a display example of an image acquired by the endoscope apparatus in FIG. 1.

In this embodiment, as shown in FIG. 3 for example, the straight-view image $G_1$ and the side-view image $G_2$ are combined at the image combining unit 20 and are displayed on the display unit 5 so that the straight-view image $G_1$ is at the inside and the side-view image $G_2$ is radially outward thereof. Accordingly, an advantage is afforded in that the straight-view image $G_1$ and the side-view image $G_2$ can be displayed in a form in which they are associated in a certain positional relationship.

Thus, with the endoscope apparatus 1 according to this embodiment, it is possible to simultaneously acquire the side-view image $G_2$, radially outward of the inserted portion 2, and the straight-view image $G_1$, frontward in the longitudinal axial direction, and it is possible to a accurately identify the position of an affected area B. Also, it is possible to acquire the fluorescence $L_2$ in the first wavelength band and the reflected light $L_4$ in the second wavelength band without loss. Therefore, it is possible to acquire a bright image with little loss of light.

According to this embodiment, a simple configuration is achieved just by disposing the dichroic conical mirror 8 in the distal end portion of the inserted portion 2, which is advantageous in that the distal end portion can be reduced in diameter.

Figure 4:
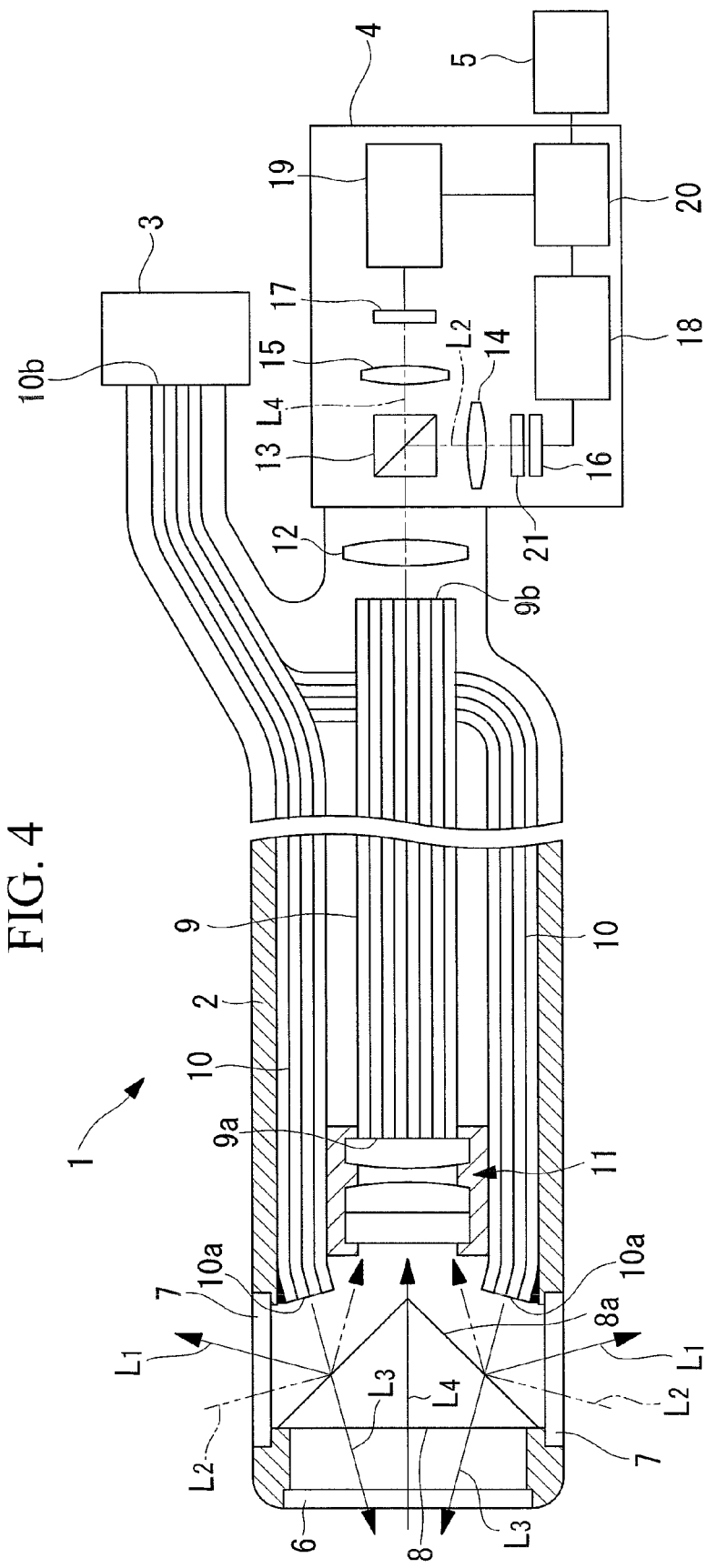
FIG. 4, which is a modification of the endoscope apparatus in FIG. 1, is an overall configuration diagram schematically showing a case where the distal ends of light guide fibers are inclined towards the center.

In the endoscope apparatus 1 according to this embodiment, an example has been shown in which the distal end faces $10a$ of the light guide fibers 10 are arranged towards the front in the longitudinal axial direction. Instead of this, however, as shown in FIG. 4, the distal end faces $10a$ of the light guide fibers 10 may be disposed so as to be inclined in a direction towards the central axis of the inserted portion 2. Doing so affords an advantage in that the intensity of the excitation light $L_1$ reflected at the dichroic conical mirror 8 and directed radially outward of the inserted portion 2 can be increased, thus enabling acquisition of a bright side-view image $G_2$.

Figure 5:
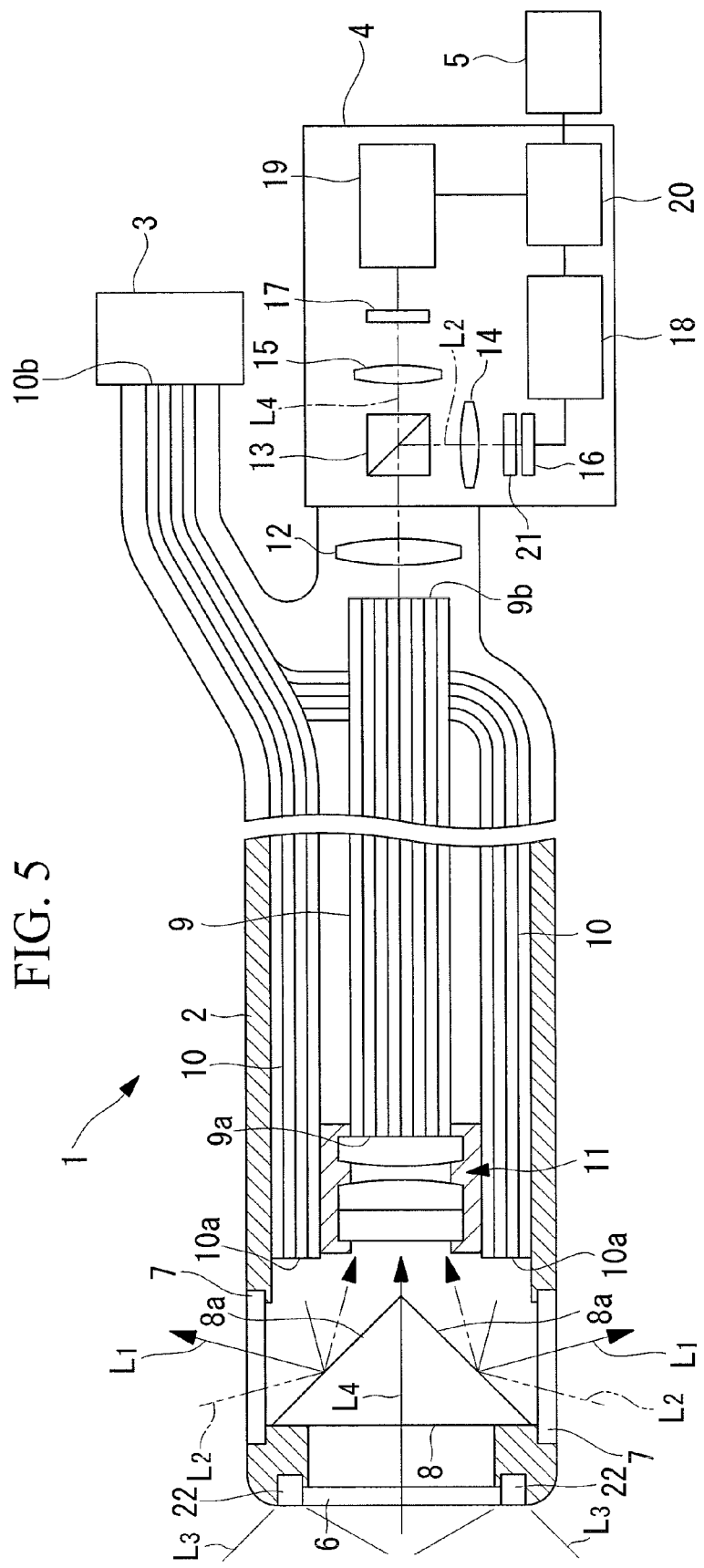
FIG. 5, which is a modification of the endoscope apparatus in FIG. 1, is an overall configuration diagram schematically showing a case where a light source for straight-view observation is included at the distal end face of the inserted portion.

In this embodiment, the excitation light $L_1$ and the illumination light $L_3$ are multiplexed in the light source 3 and guided to the distal end of the inserted portion 2 via the light guide fibers 10. Instead of this, however, as shown in FIG. 5, a light source (illumination unit) 22, such as an LED, that emits illumination light $L_3$ in the second wavelength band may be disposed at the distal end face (distal end portion) of the inserted portion, and only the excitation light $L_1$ may be guided in the light guide fibers 10 from the light source 3 at the base end of the inserted portion 2. Doing so affords an advantage in that it is possible to increase the intensity of the illumination light $L_3$ used for straight-view observation, which allows a bright straight-view image $G_1$ to be acquired. A wiring line to the light source 22 is omitted from the figure.

Figure 6:
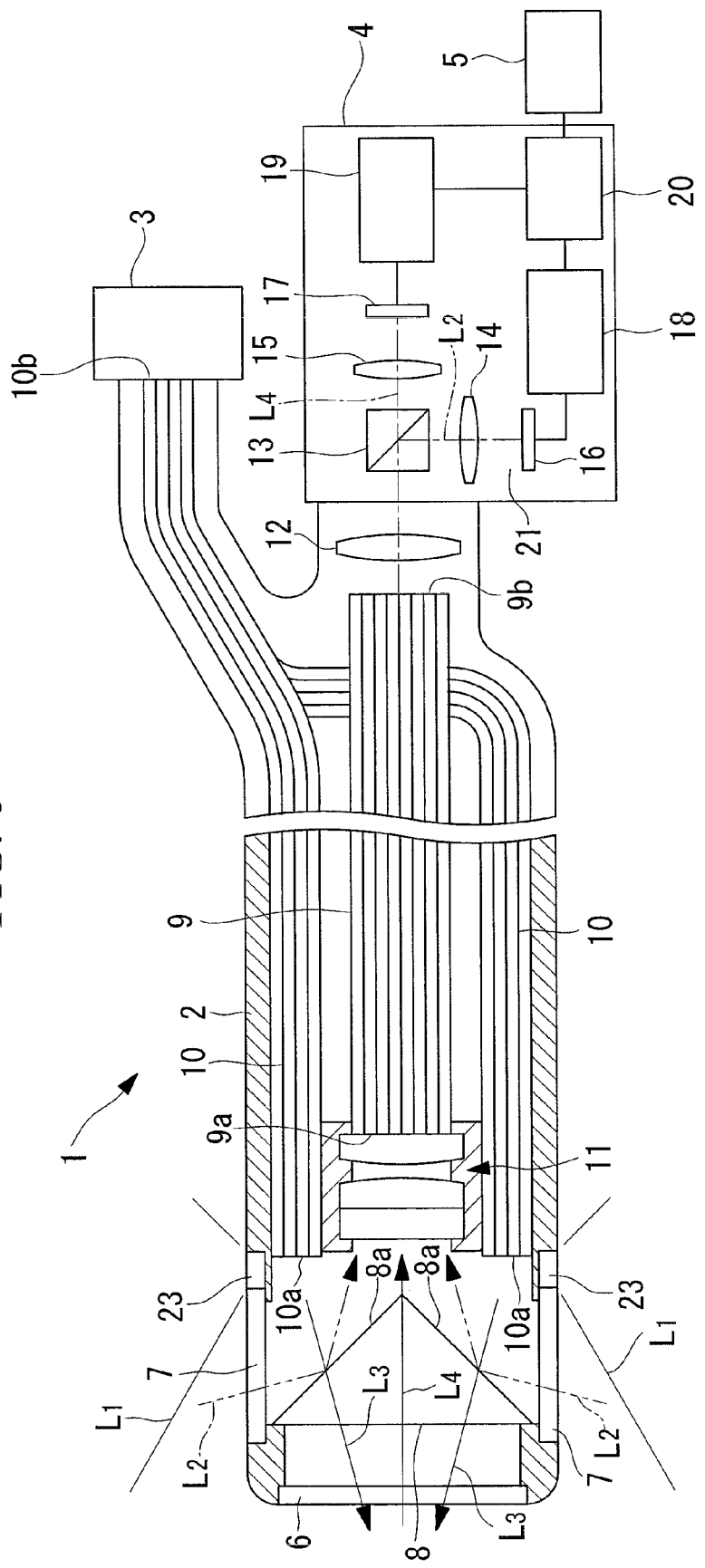
FIG. 6, which is a modification of the endoscope apparatus in FIG. 1, is an overall configuration diagram schematically showing a case where a light source for side-view observation is included at the outer periphery of the distal end portion of the inserted portion.

As shown in FIG. 6, an excitation light source 23, such as a laser diode, that emits excitation light $L_1$ in the radial direction around the outer circumferential surface of the distal end portion of the inserted portion 2 may be provided, and only the illumination light $L_3$ may be guided in the light guide fibers 10 from the light source 3 at the base end of the inserted portion 2.

Doing so affords an advantage in that the only light reflected at the dichroic conical mirror 8 is the fluorescence $L_2$, and because the excitation light $L_1$ is prevented from being reflected back, it is not necessary to provide the excitation-light cut filter 21 in the image acquisition unit 4. In addition, it is possible to widen the wavelength band that can be used for straight-view observation, making it possible to acquire an even brighter straight-view image $G_1$.

Figure 7:
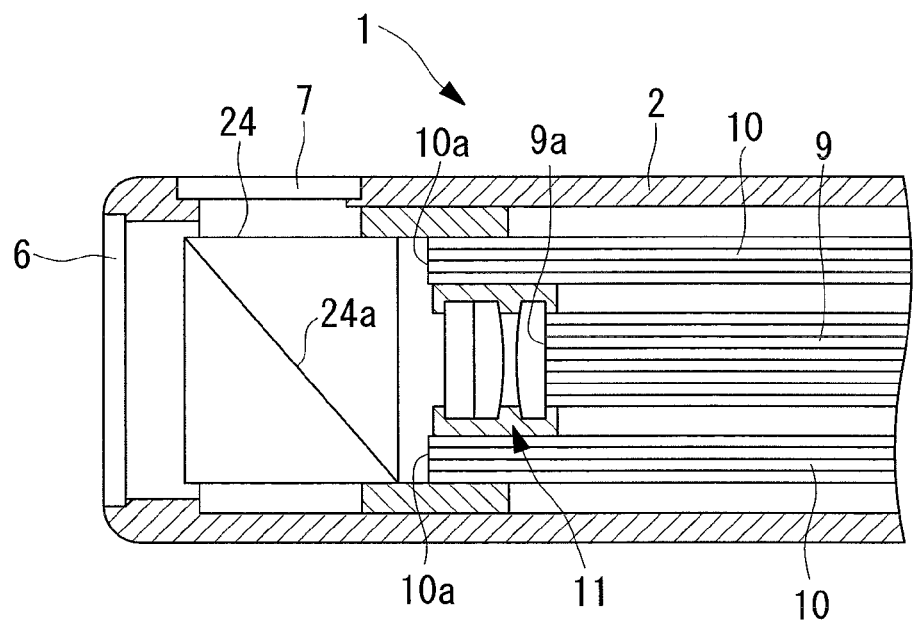
FIG. 7, which is a modification of the endoscope apparatus in FIG. 1, is a longitudinal sectional view showing the structure of the distal end portion of the inserted portion in a case where a dichroic mirror having a flat reflecting surface is provided.

In this embodiment, the dichroic conical mirror 8 is disposed at the distal end of the inserted portion 2. Instead of this, however, as shown in FIG. 7, a cuboidal dichroic mirror 24 having a flat reflecting surface $24a$ may be employed. In this case, because only an image in which the inner wall of the body cavity A is viewed from a single direction is acquired as the side-view image $G_2$, the side-view image $G_2$ covering the entire circumference should be acquired by rotating the inserted portion 2 about its longitudinal axis.

Figure 8:
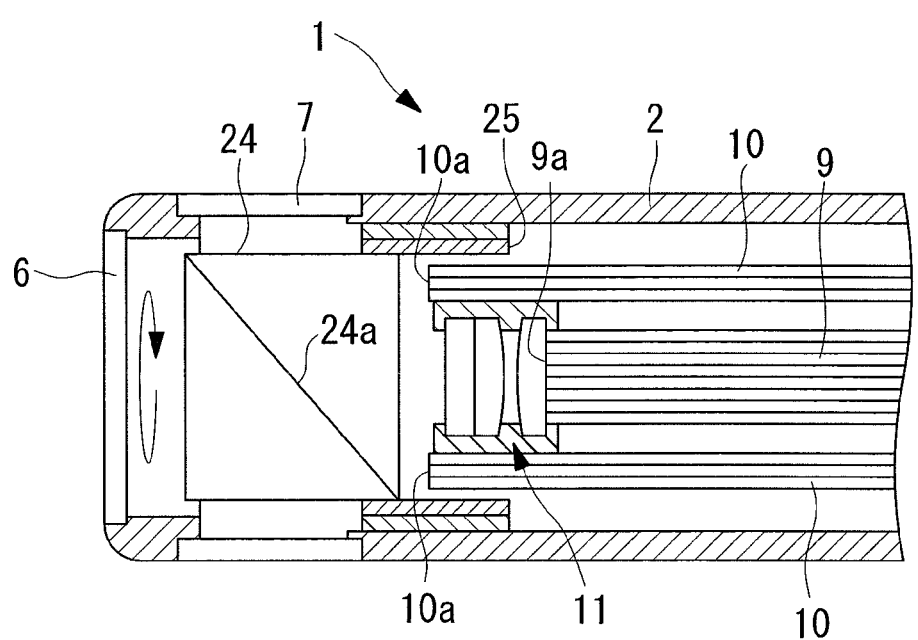
FIG. 8, which is a modification of the endoscope apparatus in FIG. 1, is a longitudinal sectional view showing the structure of the distal end portion of the inserted portion in which a dichroic mirror having a flat reflecting surface is rotated about a longitudinal axis.

Instead of this, as shown in FIG. 8, a dichroic mirror 24 having a flat reflecting surface $24a$ may be rotated about its longitudinal axis by a hollow shaft motor (rotating device) 25 provided at the distal end of the inserted portion 2.

Figure 9:
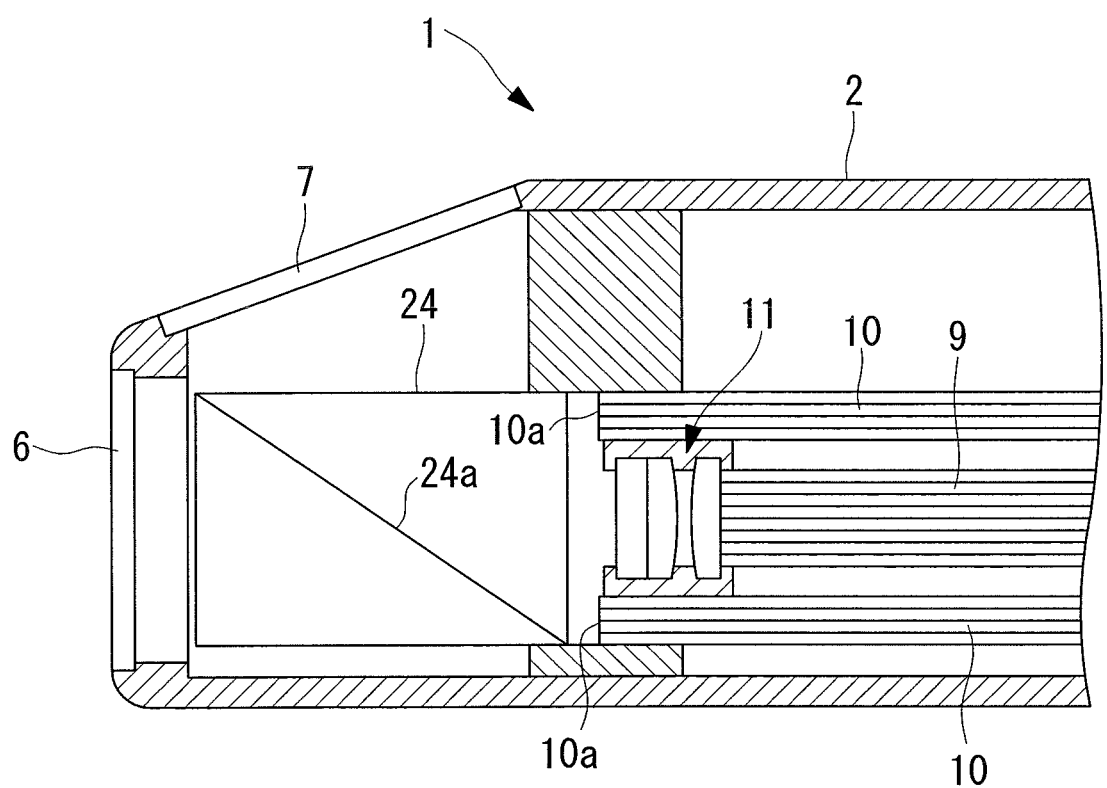
FIG. 9, which is a modification of the endoscope apparatus in FIG. 1, is a longitudinal sectional view showing the structure of the distal end portion of the inserted portion, which is capable of acquiring a frontward-inclined side-view image.

As shown in FIG. 9, by tilting the window 7 provided in the side wall of the inserted portion 2 and by setting the angle of the reflecting surface 24a of the dichroic mirror 24 to a shallow angle relative to the longitudinal axis, it is possible to acquire a side-view image $G_2$ that is inclined further frontward. Accordingly, as the straight-view image $G_1$ and the side-view image $G_2$, it is possible to acquire images at positions that are closer together inside the body cavity A.

Figure 10:
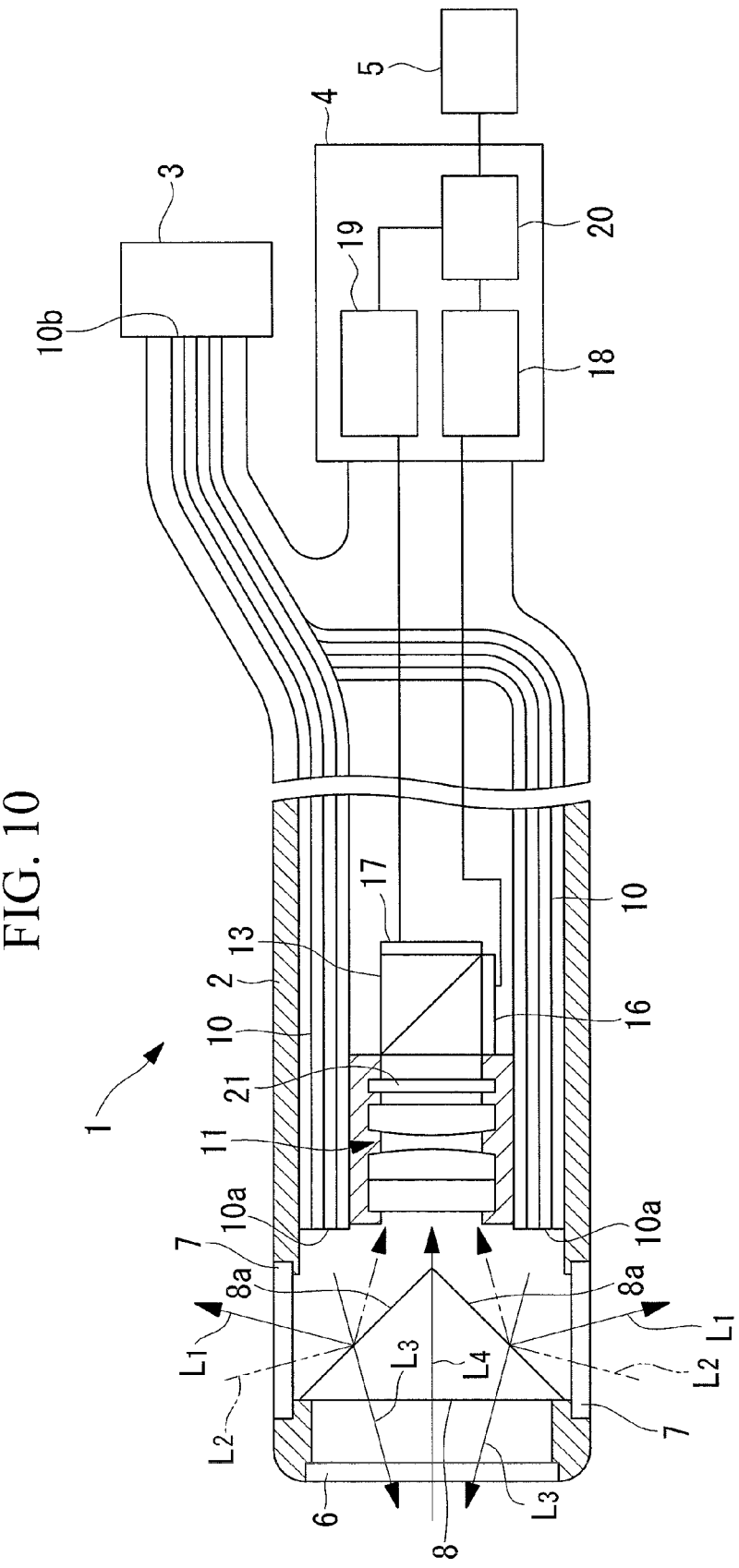
FIG. 10, which is a modification of the endoscope apparatus in FIG. 1, is an overall configuration diagram schematically showing a case where an image-acquisition device is included at the distal end of the inserted portion.

In this embodiment, a case where the image-acquisition unit 4 equipped with the image-acquisition devices 16 and 17 is disposed at the base end of the inserted portion 2 has been described. Instead of this, however, as shown in FIG. 10, the dichroic mirror 13 and the two image-acquisition devices 16 and 17 that respectively acquire light in the two wavelength bands split by the dichroic mirror 13 may be provided directly after the image-forming optical system 11. Doing so affords an advantage in that it is possible to acquire images with higher resolution than when using the image guiding fiber 9.

Figure 11:
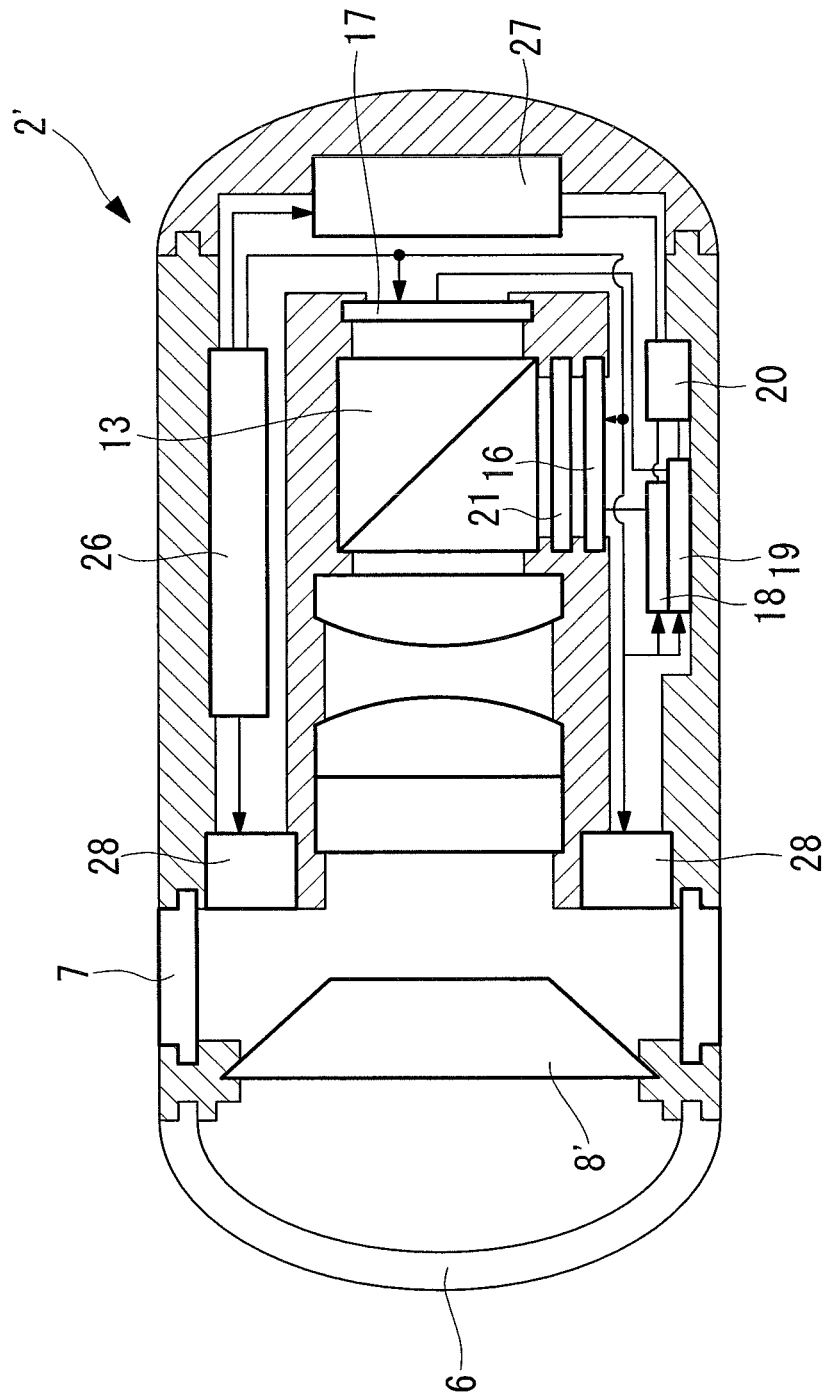
FIG. 11, which is a modification of the endoscope apparatus in FIG. 1, is a longitudinal sectional view showing a case where a first dichroic mirror is a truncated cone and the inserted portion has a capsule-shaped structure.

In the endoscope apparatus 1 according to this embodiment, a description has been given of a case where the structure of the display unit 5 etc. at the base end is integrated with the inserted portion 2. Instead of this, however, as shown in FIG. 11, a capsule-type endoscope may also be used. In this case, an inserted portion 2' is a capsule that is independent of an external apparatus (not illustrated). Because the inserted portion 2' has a structure that is independent of the external apparatus, it is internally provided with a light source 28, such a white LED. Also, a first dichroic mirror 8' has a shape formed by cutting off the tip of the first dichroic mirror 8 in the endoscope apparatus 1 according to this embodiment, that is, a truncated cone. The inserted portion 2' also includes a battery 26 for supplying power to the light source 28, such as a white LED, the image-acquisition devices 16 and 17, the side-view image generating unit 18, the straight-view image-generating unit 19, a transmitter 27, and the image combining unit 20; it is equipped with the transmitter 27 for transmitting an image signal generated in the image combining unit 20 to the external apparatus. By doing so, the burden placed on the examination subject while inserting the inserted portion 2' into the body cavity and during image acquisition is reduced. Furthermore, because the inserted portion 2' is wireless, it is possible to acquire images of and observe inside the body cavity without restricting the activity of the examination subject by the external apparatus.

The invention claimed is:

1. An endoscope apparatus comprising:
   an inserted portion to be inserted inside a body cavity;
   a first dichroic mirror, disposed in a distal end portion of the inserted portion, the first dichroic minor being configured to deflect light of a first wavelength band in a longitudinal axial direction of the inserted portion, and transmit light of a second wavelength band in the longitudinal axial direction, thereby multiplexing the light of the second wavelength band with the light of the first wavelength band, the light of the first wavelength band being incident on the first dichroic mirror in a radial direction of the inserted portion and the light of the second wavelength being incident on the first dichroic minor in the longitudinal axial direction;
   a second dichroic mirror that splits the light multiplexed by the first dichroic mirror into each of the first wavelength band and the second wavelength band; and
   two image-acquisition units that respectively acquire the light in the first and second wavelength bands split by the second dichroic mirror.

2. The endoscope apparatus according to claim 1, wherein an image combining unit that combines images acquired by the two image-acquisition units is provided.

3. The endoscope apparatus according to claim 1, wherein the first dichroic minor is conical.

4. The endoscope apparatus according to claim 1, wherein the first dichroic minor is provided with a flat reflecting surface that deflects light from one direction in the radial direction and a rotating device that rotates the reflecting surface about a longitudinal axis of the inserted portion.

5. The endoscope apparatus according to claim 1, wherein an illumination unit that radiates illumination light towards the body cavity is provided in the distal end portion of the inserted portion.

6. The endoscope apparatus according to claim 1, wherein
   an illumination unit that radiates illumination light towards the body cavity is provided; and
   the illumination unit includes a light source disposed at a base end of the inserted portion and a light guide through which light from the light source propagates to the distal end of the inserted portion.

7. The endoscope apparatus according to claim 6, wherein:
   an image-forming unit that images the light multiplexed by the first dichroic minor is provided at a central portion, in the radial direction, of the inserted portion;
   the light guide is disposed outward, in the radial direction, of the image forming unit; and
   the distal end of the light guide is disposed at an angle towards the vicinity of the center of the first dichroic mirror.

8. The endoscope apparatus according to claim 1, wherein the inserted portion is a capsule provided, in the interior thereof, with the first dichroic mirror, the second dichroic minor, and the two image-acquisition units.

* * * * *